(12) United States Patent
Xu et al.

(10) Patent No.: US 11,925,669 B2
(45) Date of Patent: Mar. 12, 2024

(54) CHINESE HERBAL MEDICINE COMPOSITION HAVING A FUNCTION OF REDUCING URIC ACID

(71) Applicant: Infinitus (China) Company Ltd., Jiangmen (CN)

(72) Inventors: Xiaofei Xu, Guangzhou (CN); Xiaolei Guo, Guangzhou (CN); Chungwah Ma, Guangzhou (CN); Bin Shi, Guangzhou (CN); Zhen Luo, Guangzhou (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 1933 days.

(21) Appl. No.: 14/142,930

(22) Filed: Dec. 30, 2013

(65) Prior Publication Data

US 2014/0212519 A1    Jul. 31, 2014

(30) Foreign Application Priority Data

Jan. 30, 2013 (CN) .......................... 201310035005.3

(51) Int. Cl.
| | | |
|---|---|---|
| *A61K 36/00* | (2006.01) | |
| *A61K 36/28* | (2006.01) | |
| *A61K 36/488* | (2006.01) | |
| *A61K 36/68* | (2006.01) | |
| *A61K 36/8994* | (2006.01) | |
| *A61K 36/90* | (2006.01) | |

(52) U.S. Cl.
CPC ............ *A61K 36/28* (2013.01); *A61K 36/488* (2013.01); *A61K 36/68* (2013.01); *A61K 36/8994* (2013.01); *A61K 36/90* (2013.01)

(58) Field of Classification Search
CPC .... A61K 36/28; A61K 36/8994; A61K 36/90; A61K 36/48
USPC .......................... 424/738, 776, 773, 750, 757
See application file for complete search history.

(56) References Cited

U.S. PATENT DOCUMENTS 7,812,004 B2 * 10/2010 Frippiat ................ A23L 29/244
514/54

FOREIGN PATENT DOCUMENTS

| CN | 101074417 A | * | 11/2007 |
| CN | 102462795 A | * | 5/2012 |
| JP | 2007016053 A | * | 1/2007 |

OTHER PUBLICATIONS

English machine translation of Qu et al., CN 1362059 A, 2002.*

* cited by examiner

*Primary Examiner* — Rosanne Kosson
(74) *Attorney, Agent, or Firm* — JCIPRNET

(57) ABSTRACT

Herbal composition having an effect of reducing uric acid, which is made from the following herbal materials in specified portions by weight: 4-30 portions of Glabrous greenbrier rhizome, 2-15 portions of Chicory, 2-15 portions of Herba *Plantaginis*, 2-20 portions of *Coix* seed, and 2-10 portions of Kudzuvine Root. The composition may be used in combination with modern Western medicines to achieve optimal effects.

9 Claims, No Drawings

CHINESE HERBAL MEDICINE COMPOSITION HAVING A FUNCTION OF REDUCING URIC ACID

CROSS-REFERENCE TO RELATED APPLICATIONS

This application claims priority from CN Application No. 201310035005.3, filed Jan. 30, 2013, the contents of which are incorporated herein in the entirety by reference.

FIELD OF THE INVENTION

The present invention relates to a Chinese herbal composition, and in particular relates to a health-care dietary product having a function of reducing uric acid, with Chinese herbal medicine as the main raw materials.

Thought the specification of the present invention, reference is made to the theory and practice in Traditional Chinese Medicine and it is believed that such reference may help explain the beneficial effects observed in the present invention and provide some guidance for those of ordinary skill in the art to make modifications based on the spirit of the present invention. However, it is it is understood that the applicant is not bound by the TCM theory and practice referenced and emphasis should be placed on the actual effects observed in the experiments described herewith.

BACKGROUND OF THE INVENTION

According to the Traditional Chinese Medicine (TCM), the cause of hyperuricemia is Congenital Kidney Deficiency, Zheng Qi becoming deficient, or the functions of Qi transformation and dispersion of Water Humor becoming weak. Moreover, Acquired Constitution is influenced by overeating fat meat, fine grain and strong flavors, so Spleen and Stomach are hurt, which causes the transformation of Water-Dampness abnormal, the pathogenic Dampness-Turbidity descend and be viscous and stagnated in viscera. Qi movement then is stagnated, hereby rendering the Ascending-Descending of Qi movement unregulated, dispelling of urine and Turbidity disordered, Turbidity and Stasis stagnated in the channels, network vessels and joints, Dampness and Turbidity brewing internally, and the movement of Qi and Blood being out of control. Consequently, Phlegm, Dampness and Stasis are produced. Vice versa, when Blood movement is stagnated, Dampness is unable to be coagulated, the production of Phlegm, Dampness and Stasis is worsened. The obstruction of channels and network vessels by Phlegm, Dampness and Stasis is mainly due to pathogenic excess complicated with deficiency of source. According to this TCM theory, the treatment shall emphasize on fortifying Spleen, freeing the network vessels, and removing Dampness and draining Turbidity.

TCM theory further believes that treating Dampness without dealing with dysuria is not a really useful. Thus, it would be effective by adding the treatment with the components that can fortify Spleen, remove Dampness and drain Turbidity. When the movement of Spleen Qi is fortified, Dampness and Turbidity can not be generated internally, and at the same time the already generated Dampness and Turbidity will be drained through urine and feces. By dispelling pathogen, Dampness is expelled, which renders already formed pathogenic Heat removed and prevents Phglem and fluid retention, so as to treat both the manifestation and the underlying cause of the disease.

SUMMARY OF THE INVENTIONS

The present invention provides a Chinese herbal composition having a function of reducing uric acid, and a health-care dietary product prepared from such Chinese herbal composition (with or without being further supplemented by other Chinese herbal medicine or food additives), which has a significant effect on reducing uric acid as well as promoting overall health for sub-healthy people.

The Chinese herbal composition having a function of reducing uric acid according to the present invention is prepared from herbal components in the following portions by weight: 4-30 portions of Glabrous greenbrier rhizome (Rhizoma Smilacis Glabrae), 2-15 portions of Chicory (*Cichorium intybus* L.), 2-15 portions of Herba *Plantaginis*, 2-20 portions of *Coix* seed (Semen Coicis), 2-10 portions of Kudzuvine Root (Radix *Puerariae*).

More preferably, the herbal composition of the present invention comprises: 10-25 portions of Glabrous greenbrier rhizome, 5-12 portions of Chicory, 3-12 portions of Herba *Plantaginis*, 6-18 portions of *Coix* seed, and 4-8 portions of Kudzuvine Root.

The most preferably, the herbal composition of the present invention comprises: 20 portions of Glabrous greenbrier rhizome, 15 portions of Chicory, 8 portions of Herba *Plantaginis*, 12 portions of *Coix* seed, and 8 portions of Kudzuvine Root.

The aforesaid herbal composition having a function of reducing uric acid is preferably in the form of a health-care dietary product, which may be prepared in many different dosage forms using conventional formulation techniques. For example, the dosage forms can be oral liquid, capsule, tablet, powder or granule, etc.

Glabrous greenbrier rhizome, is the dried root of Glabrous greenbrier rhizome Roxb., which is the plant of Liliaceae. According to TCM, it has a nature and flavor of Sweetness, Blandness and Balance, belongs to Liver and Stomach Channels, its effect is for dehumidification, detoxification, and freeing the joints, and its dosage amount is 15-60 g according to the "Chinese Pharmacopoeia". Glabrous greenbrier rhizome has a nature of Sweetness, Blandness and Balance, it is nontoxic, inexpensive and effective, thus is a key medicine for dehumidification, detoxification, and freeing the joints, and is a traditional medicine material but is also edible as dietary material.

Chicory, is the aboveground part of Cichorium glandulosum Boiss.et Hout and *Cichorium intybus* L, which are the plants of Compositae. This herbal is a common medicine of uighurs, according to the "Chinese Pharmacopoeia", it has a nature and flavor of Bitterness, Saltiness, and Cold, its effect is for clearing Liver and uninhibiting Gallbladder, fortifying Spleen and digesting food, diuresis and dispersing swelling, its dosage amount is 9-18 g. It has a clinical therapeutic effect on the hyperlipidaemia and hyperglycemia caused by encumbrance of Dampness-Heat, secondary infection and pain caused by downpour of Dampness-Heat.

Herba *Plantaginis*, is the dried whole grass of *Plantago asiatica* L. or *Plantago* depressa Willd, which are the plant of Plantaginaceae. Herba *Plantaginis* has a nature and flavor of Sweetness and Cold, belongs to Liver, Kidney, Lung, and Small intestine Channels. Its effect is for clearing Heat and Diuresis, dispelling Phlegm, cooling Blood, and detoxification. It is used for treating adema and urine shortage, Heat Strangury and rough and pain, summerheat-Dampness and diarrhea, Phlegm-Heat and coughing, Blood ejection and spontaneous external bleeding, swelling and toxin of welling-abscess and sores, and its dosage amount is 9-30 g.

*Coix* seed, is the dried mature seed of *Coix lacryma-jobi* L. var. ma-yuen (Roman.) Stapf, which is the plant of Gramineae. *Coix* seed has a nature and flavor of Sweetness, Blandness and Cold, belongs to Spleen, Stomach, and Lung Channels, its effect is for disinhibiting Water and percolating Dampness, fortifying Spleen and against diarrhea, eliminating impediment, expelling pus, detoxification and dissipating binds, its dosage amount is 9-30 g. Its nature is mild and cold but does not hurt stomach, it fortifies Spleen but is not rich or slimy, it soothes sinews and against impediment but does not hurt Yin. It is used for treating the adema, inhibited urination, and beriberi caused by spleen deficiency, for treating exuberant dampness, spleen deficiency and diarrhea, and impediment pattern etc.

Kudzuvine Root, is the dried root of *Pueraria* lobata (Willd.) Ohwi or *Pueraria thomsonii* Benth, which are the plant of Leguminosae. Kudzuvine Root has a nature and flavor of Sweetness, Acridity and Cold, belongs to Spleen and Stomach Channels. Its effect is for resolving the flesh and abating fever, engendering liquid, outthrustnig papules, upbearing Yang and against diarrhea. It is used for treating external contraction fever and headache, rigidity and pain of neck and back, dispersion-thirsty, non-eruption of meales, heat dysentery, and diarrhea.

The Chinese herbal medicine composition having a function of reducing uric acid according to the present invention, comprises Glabrous greenbrier rhizome, Chicory, Herba *Plantaginis, Coix* seed, and and Kudzuvine Root as components. Among them, Glabrous greenbrier rhizome has the flavor and taste of Sweetness, Blandness and Balance, belongs to Liver and Stomach Channels, with effects of dehumidification, detoxification, and freeing the joints, thus it is the monarch drug; Chicory has the flavor and taste of mild Bitterness, Saltiness, and Cold, with effects of clearing Liver and uninhibiting Gallbladder, fortifying Spleen and digesting food, diuresis and dispersing swelling; Herba *Plantaginis* has the effects of clearing Heat and Diuresis, cooling Blood and detoxification, thus said components are combined to be ministerial drugs; *Coix* seed has the effects of disinhibiting Water and percolating Dampness, fortifying Spleen and againt diarrhea, and detoxification, thus is an adjuvant drug; Kudzuvine Root has the effects of engendering liquid and against thirsty, freeing the channels and quickening the network vessels, thus is a conductant drug. These medicines are co-administered to achieve the effect of fortifying Spleen and disinhibiting dampness, clearing Heat, and freeing the joints. Referring to modern pharmaceutical researches in combined with clinical reports, each component in the composition has an effect of reducing the serum level of uric acid, anti-inflammation, analgesis, thus is suitable for primary hyperuricemia patients. The Chinese herbal medicine composition of the present invention are characterized by using five Chinese herbal medicines being Glabrous greenbrier rhizome, Chicory, Herba *Plantaginis, Coix* seed, and Kudzuvine Root as major components, through optimal formulation and co-adminstration, so as to achieve the effect of reducing uric acid from various pathways and levels.

The present invention will be further illustrated by the results of the specific embodiments and pharmacodynamic studies described in the following.

DETAILED DESCRIPTION OF PARTICULAR EMBODIMENTS OF THE INVENTION

The present invention is described in connection with some specific embodiments illustrated as follows. It is understood that the following specific examples are only intended to further illustrate the present invention and shall not be deemed to limit the protection scope of the present invention. Some non-substantial modifications and adjustments made by the others according to the spirit of the present invention shall fall into the scope of the invention.

Example 1

The health-care dietary product of Example 1 of the present invention, is prepared from the components in the following portions by weight: 20 portions of Glabrous greenbrier rhizome, 15 portions of Chicory, 8 portions of Herba *Plantaginis,* 12 portions of *Coix* seed, and 8 portions of Kudzuvine Root.

Example 2

The health-care dietary product of Example 2 of the present invention, is prepared from the components in the following portions by weight: 8 portions of Glabrous greenbrier rhizome, 15 portions of Chicory, 15 portions of Herba *Plantaginis,* 10 portions of *Coix* seed, and 10 portions of Kudzuvine Root.

Example 3

The health-care dietary product of Example 3 of the present invention, is prepared from the components in the following portions by weight: 20 portions of Glabrous greenbrier rhizome, 15 portions of Chicory, 13 portions of Herba *Plantaginis,* 10 portions of *Coix* seed, and 8 portions of Kudzuvine Root.

Example 4

The health-care dietary product of Example 4 of the present invention, is prepared from the components in the following portions by weight: 18 portions of Glabrous greenbrier rhizome, 13 portions of Chicory, 10 portions of Herba *Plantaginis,* 17 portions of *Coix* seed, and 7 portions of Kudzuvine Root.

Example 5

The health-care dietary product of Example 5 of the present invention, is prepared from the components in the following portions by weight: 15 portions of Glabrous greenbrier rhizome, 10 portions of Chicory, 8 portions of Herba *Plantaginis,* 15 portions of *Coix* seed, and 5 portions of Kudzuvine Root.

Example 6

The health-care dietary product of Example 6 of the present invention, is prepared from the components in the following portions by weight: 25 portions of Glabrous greenbrier rhizome, 12 portions of Chicory, 12 portions of Herba *Plantaginis,* 15 portions of *Coix* seed, and 6 portions of Kudzuvine Root.

Example 7

The health-care dietary product of Example 7 of the present invention, is prepared from the components in the following portions by weight: 15 portions of Glabrous greenbrier rhizome, 8 portions of Chicory, 10 portions of Herba *Plantaginis,* 18 portions of *Coix* seed, and 8 portions of Kudzuvine Root.

All herbal ingredients in the aforesaid examples are "off the shelf" commercial products, prepared in various forms through conventional formulation techniques (such as water extraction and alcohol extraction, etc.), and formulated into many pharmaceutical dosage forms, such as oral liquid, capsule, tablet, powder or granule, etc.

Pharmacodynamic Studies

Using the composition of Example 1, in the form of an oral liquid formulation (the testing sample) prepared by the conventional water extraction method, the efficacy was demonstrated in a way described as follows:

1. Experimental Site

Department of Pharmacology & Toxicology, School of Pharmaceutical Sciences, Sun Yat-Sen University, Guangzhou, China.

2. Experimental Purpose

Examine the effect of the Chinese herbal composition of the present invention for reducing uric acid in the rat model of hyperuricemia.

3. Laboratory Animals 3.1 Grade and germ line: SPF-Grade SD Rat 3.2 Animal management: the animals were fed and looked after by the staff having a qualification certificate for laboratory animal management.

3.3 Purchase date: Jul. 10, 2012, of an age around 6-week.

3.4 Body weight, number, and gender at purchase: 50 males with body weights in the range of 130-150 grams.

3.5 Breeding site: the Laboratory Animal Center of Guangzhou University of Chinese Medicine (Laboratory Animal Production License No is SCXK(YUE) 2008-0020). The Laboratory Animal Quality Certificate No. is 0110322.

3.6 Immunization: immunized rats were examined for 3 days, during which, indicators such as the appearance, activities, excrement character, weight and diet of the animal are observed.

3.7 Reason for selecting rats as the test animals: Rats are strong in fertility, easily fed, with a size suitable for easy administration, and are convenient for sampling and quantification, making them suitable for this study.

3.8 Animal-labeling: Dots are painted on different sites of hair on the body surface of animals, with saturated picric acid solution, to indicate different number references.

3.9 Cage-labeling: The filled label card (indicating experiment title, special person in charge, animal's germ line, gender, numbering, grouping, prescription start date, etc.,) is hung on the front surface of the rat cage.

4. Feeding and Management of Animals

Feeding Room: Barrier animal facilities on 2nd floor, Laboratory Animal Center (Northern Campus), Sun Yat-Sen University. Laboratory animal Usage License No. SYXK (YUE) 2007-0081.

Temperature: 20~25° C.; Humidity: 40%~70%

Aeration times: more than 10 times/hour

Feeding density: 5/cage

Illumination Duration: 12 hrs (turn on at 7am, turn off at 7pm)

5. Feedstuff

Type: Sterile feedstuff for SPF-grade rats, manufactured by Guangdong Medical Lab Animal Center, address: Huang Qi BoYang Road No. 119, Nanhai District, Foshan City, Production License No. is SCXK (YUE) 2008-0002.

Feeding method: Freely ingested

Conventional nutritional component index of feedstuff: as determined by Guangdong Laboratory Animals Monitoring Institute (Referring to National Standard of the People's Republic of China GB14924.3-2010), inspection frequency: twice yearly.

Storage of feedstuff: stored in a particular storeroom, keep ventilated, clean, dry.

6. Drinking Water

Type: sterile water sterilized under 121° C. (1.0kg/cm$^2$) for 30 min, complying with Water quality standard for fine drinking water (CJ94-2005).

Administration method: Freely ingested through animal drinking bottles.

7. Equipment and Reagents

Equipment

Electric balance: PUT, manufactured by Shenzhen Amput Electronic Technology Co., Ltd;

Electric balance: mettler Toledo, Type: p1303;

Table-top centrifuge: LDZ5-2 centrifuge, manufactured by Beijing medical centrifuge factory;

DK-80 type electric heating water bath, manufactured by electric heating water bath, manufactured by Guangdong Huankai Microbial Sci. & Tech. Co. Ltd.;

W-80A votex, manufactured by Shanghai Medical University Instrument Factory; BECKMAN Synchron CX5 Chemistry Analyzer (USA);

Miscellaneous: Fixing cage, capillary blood-sampling tube, centrifuge tube, syringe etc.

Reagents

Uric Acid Test Kit (enzymatic colorimetry): Lot number: T20120310, manufactured by Fenghui (S.H.) Medical Science & Tech. Company Ltd.

8. Experimental Design

Animal grouping

Animals were assigned randomly into: Blank control group, Sample control group, Model control group, Test group, and Positive control group. Each group consisted of 10 animals.

Administration

Administration route and reason: orally intragastrical administration, as it is similar to clinical administration route.

Administration frequency: once daily.

Dosage of intragastrical sample: administrated in the amount 30 folds of human body's recommended dosage (20 g/d of raw material), the equivalent dosage for rat (calculated as concentrated solution) 50÷60×30×2÷3=16.67(ml/kg/d), is about 17 ml/kg/d.

Administration amount: 1.7 ml/100 g rat.

9. Experimental Methods 50 healthy male SD rats, body weights in the range of 130-150 g, were observed for 3 days in the experimental environment upon normal feeding and immunization. They were randomly assigned into 5 groups, each group consisting of 10 animals, the body weight distribution of each group of rats is similar. These groups were Blank control group (distilled water-17 ml/kg), Sample control group (17 ml/kg), Model control group (distilled water-17 ml/kg), Test group (test sample-17 ml/kg), Positive control group (allopurinol), respectively. Blank control group was administrated with 17 ml/kg of distilled water intragastrically every afternoon, Sample control group was administrated with 17 ml/kg of test sample intragastrically every afternoon, Model control group was administrated with distilled water intragastrically in the afternoon, Positive control group was administrated with allopurinol intragastrically in the afternoon, and Test group was administrated with 17 ml/kg of test sample intragastrically in the afternoon. Additionally, for Model control group, Positive control group and Test group, each group was administrated with Oteracil potassium intragastrically every morning. The administration was conducted daily for 30 days. Prior to experiments, the rats were fastened for 12 h (but water was provided) and then about 1 ml of blood were taken from orbital veniplex with glass capillary tube. Sera were separated for measuring the pre-testing level of uric acid. On day 30, blood were taken in the same manner and sera were separated for measuring the serum levels of uric acid, creatinine, and urea nitrogen.

Modeling principle: Rats were intragastrically administrated with Oteracil potassium, a chemical inhibitor of uricase, to inhibit the activity of uricase in the body of rats, rendering uric acid in the body of rats unable to breakdown, causing the accumulation of uric acid produced in the serum, so as to produce a rat model of hyperuricemia.

Animal grouping and administration

Blank control group: 17 ml/kg*d of distilled water was administrated intragastrically, once daily for 30 days;

Sample control group: 17 ml/kg*d of test sample was administrated intragastrically, once daily for 30 days;

Model control group: 17 ml/kg*d of distilled water was administrated intragastrically, once daily for 30 days;

Test sample prevention group: 17 ml/kg*d of test sample was administrated intragastrically, once daily for 30 days;

Positive control group: 17 ml/kg*d of positive control allopurinolis administrated intragastrically, once daily for 30 days.

10. Observation Indicators

General status observation: The status of animals (appearance, activities, excrement character, diet conditions etc) were observed daily.

11. Data Processing

ANOVA (analysis of variance) was used. Firstly, homogeneous variance test was carried out, and F values were calculated. If F value<$F_{0.05}$, it indicated that the means of each group had no significant difference; if F value≥$F_{0.05}$, P≤0.05, the mean of each experimental group and control group were compared for statistical analysis; for non-normal or heterogeneous variance data, appropriate variant transformation was processed, when normal or homogeneous variance requirement was satisfied, the transformed data was processed for statistical analysis; if normal or homogeneous variance requirement could not satisfied after variant transformation, Rank sum test was used for statistical analysis.

12. Experimental Results 12.1 General status observation

In comparison with Blank control group, all other groups of animals showed less smooth hair, but had no significant difference in other appearance signs, activities, and excrement characters etc. In comparison with Model control group, Test group and Positive control group had no significant difference in appearance, activities, and excrement characters etc.

12.2 Observation of body weight

As shown in Table 1, the serum levels of uric acid (UA), urea nitrogen (BUN), and creatinine (CR) of each group of rats prior to modeling (i.e., prior to administration) were essentially similar, and they had no significant difference between groups (comparing with Blank control group or Model control group, each p>0.05). It meant that each group of rats have similar levels of relevant metabolism indicators in serum prior to modeling (prior to administration).

TABLE 1

UA, BUN, CR contents in the sera of rats prior to administration ($\overline{X} \pm S$)

| Grouping | n | BUN (μmol/L) | CR (mmol/L) | UA (μmol/L) | UA Reduction (%) |
|---|---|---|---|---|---|
| Blank control group | 10 | 8.01 ± 2.17 | 29.40 ± 7.10 | 48.20 ± 14.43 | |
| Sample control group | 10 | 6.19 ± 1.88 | 24.60 ± 11.22 | 54.30 ± 14.97 | / |
| Model control group | 10 | 9.68 ± 2.13 | 33.10 ± 8.20 | 54.00 ± 14.82 | / |
| Test sample prevention group | 10 | 10.41 ± 2.58 | 31.70 ± 10.28 | 53.30 ± 15.70 | / |
| Positive control group | 10 | 8.82 ± 2.72 | 28.90 ± 5.17 | 51.10 ± 9.21 | / |

Notes:
Comparing to Blank control group, each group is p > 0.05;
Comparing to Model control group, each group is p > 0.05.

Observation of Body weight: The growing condition of animals were observed by weighing prior to administration and on Day 30 of administration.

Observation of relevant metabolism indicators:

Blood were taken prior to administration and on Day 30 of administration to measure uric acid, creatinine, urea nitrogen, to calculate the changing rate of uric acid level in serum.

The changing rate of uric acid in serum=(uric acid value in serum after experiment-uric acid value in serum prior to experiment)/uric acid value in serum prior to experiment×100%

As it can be seen from Table 2, each group of rats had essentially similar body weights prior to modeling (prior to administration), because grouping is randomly assigned with respect to body weights. After continuous feeding for 10 days (10 d), 20 days (20 d) and 30 days (30 d), each group of rats gained weight. Upon 10 d feeding, comparing with Blank control group, the other groups of rats grew faster but had no statistical difference (p>0.05); upon 20 d feeding, comparing with Blank control group, the other groups of rats grew faster but still had no statistical difference (p>0.05); upon 30 d feeding, comparing with Blank control group, the body weights of each other group of rats had no statistically difference either (p>0.05).

TABLE 2

Effects on body weights of each group of rats ($\overline{X} \pm S$)

| Grouping | n | Weight prior to administration (g) | 10 d weight (g) | 20 d weight (g) | 30 d weight (g) |
|---|---|---|---|---|---|
| Blank control group | 10 | 145.4 ± 15.3 | 173.2 ± 20.0 | 204.5 ± 18.7 | 241.9 ± 17.2 |
| Sample control group | 10 | 145.7 ± 23.8 | 185.4 ± 25.3 | 210.8 ± 32.0 | 238.0 ± 36.4 |
| Model control group | 10 | 144.6 ± 15.7 | 191.2 ± 18.0 | 215.5 ± 19.4 | 244.6 ± 22.8 |
| Test sample prevention group | 8-10 | 145.9 ± 12.0 | 190.1 ± 15.7 | 222.0 ± 26.4 | 236.25 ± 32.9 |
| Positive control group | 10 | 143.5 ± 11.4 | 185.7 ± 15.9 | 224.2 ± 21.8 | 254.4 ± 23.1 |

Notes:
Comparing to Blank control group, each group is p > 0.05;
Comparing to Model control group, each group is p > 0.05.

TABLE 3

UA, BUN, CR levels in the sera of rats upon 30 d administration ($\overline{X} \pm S$)

| Grouping | n | BUN (μmol/L) | CR (mmol/L) | UA (μmol/L) | UA Reduction (%) |
|---|---|---|---|---|---|
| Blank control group | 10 | 5.97 ± 1.06 | 36.30 ± 6.03 | 73.10 ± 21.86 | / |
| Sample control group | 10 | 5.06 ± 0.57# | 42.40 ± 3.77# | 67.70 ± 25.67 | ↓7.4 |
| Model control group | 10 | 5.34 ± 0.64 | 38.20 ± 7.53 | 135.50 ± 19.57## | / |
| Test sample prevention group | 8 | 5.24 ± 0.96 | 40.25 ± 7.69 | 106.63 ± 24.4* | ↓21.3 |
| Positive control group | 10 | 5.53 ± 0.79 | 40.40 ± 7.32 | 63.20 ± 17.19** | ↓53.4 |

Notes:
Comparing to Blank control group,
$p < 0.05$,
$p < 0.01$;
Comparing to Model control group,
*indicates $p < 0.05$,
**indicates $p < 0.01$;
the reduction of Sample control group is calculated in comparison with Blank control group, the reduction of other groups are calculated in comparison with Model control group.

It is seen from Table 3 that, upon 30 d Administration (30 d modeling), in comparison with Blank control group, Sample control group: UA level showed some reduction (7.4%) but without a statistic significance, BUN showed an increase(p<0.01), and CR level showed no significant change (p>0.05); Model control group: UA showed an significantly increase (p<0.01) (as the UA level of Blank control group was 73.10±21.86 μmol/L while UA level of Model control group was 135.50±19.57 μmol/L), changes in BUN and CR levels in sera were not significant (p>0.05). In comparison with Model control group, Test group showed a significant reduction in blood UA level (p<0.05), with a changing rate of ↓21.3%; Positive control group (with allopurinol) also showed a significant reduction in blood UA level significantly (p<0.01) with a changing rate of ↓53.4%.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

CONCLUSION

Upon 30 d oral administration of the test sample, in comparison with Model control group, the uric acid value of serum was significantly reduced, having a statistical significance (p<0.05), which indicates that said test sample has an effect of reducing uric acid.

What is claimed is:
1. An herbal composition having an effect of reducing uric acid, comprising therapeutically effective amounts of the following herbal ingredients in specified weight portions: 4-30 portions of Glabrous greenbrier rhizome, 2-15 portions of Chicory, 2-15 portions of Herba *Plantaginis,* 2-20 portions of *Coix* seed, and 2-10 portions of Kudzuvine Root.

2. The herbal composition of claim 1, wherein said ingredients are in following specified weight portions: 10-25 portions of Glabrous greenbrier rhizome, 5-12 portions of Chicory, 3-12 portions of Herba *Plantaginis,* 6-18 portions of *Coix* seed, and 4-8 portions of Kudzuvine Root.

3. The herbal composition of claim 2, wherein said ingredients are in following specified weight portions: 20 portions of Glabrous greenbrier rhizome, 15 portions of Chicory, 8 portions of Herba *Plantaginis,* 12 portions of *Coix* seed, and 8 portions of Kudzuvine Root .

4. A healthcare dietary product, comprising therapeutically effective amounts of extracts from following herbal ingredients in specified weight portions: 4-30 portions of Glabrous greenbrier rhizome, 2-15 portions of Chicory, 2-15 portions of Herba *Plantaginis*, 2- 20 portions of *Coix* seed, and 2-10 portions of Kudzuvine Root.

5. The healthcare dietary product of claim 4, wherein wherein said ingredients are in following specified weight portions: 10-25 portions of Glabrous greenbrier rhizome, 5-12 portions of Chicory, 3-12 portions of Herba *Plantaginis*, 6-18 portions of *Coix* seed, and 4-8 portions of Kudzuvine Root.

6. The healthcare dietary product of claim 4, wherein 20 portions of Glabrous greenbrier rhizome, 15 portions of Chicory, 8 portions of Herba *Plantaginis,* 12 portions of *Coix* seed, and 8 portions of Kudzuvine Root .

7. The healthcare dietary product of claim 4, which is formulated into a dosage form selected from the group consisting of oral liquid, capsule, tablet, powder and granule.

8. The healthcare dietary product of claim 5, which is formulated into a dosage form selected from the group consisting of oral liquid, capsule, tablet, powder and granule.

9. The healthcare dietary product of claim 6, which is formulated into a dosage form selected from the group consisting of oral liquid, capsule, tablet, powder and granule.

\* \* \* \* \*